US012661498B2

(12) United States Patent
Alwatban et al.

(10) Patent No.: US 12,661,498 B2
(45) Date of Patent: Jun. 23, 2026

(54) ADAPTIVE FLOW CALCULATION FOR A MECHANICAL CIRCULATORY SUPPORT DEVICE

(71) Applicant: Abiomed, Inc., Danvers, MA (US)

(72) Inventors: Mohammed Alwatban, Danvers, MA (US); Ahmad El Katerji, Danvers, MA (US); Maxim Daschewski, Berlin (DE); Gerd Spanier, Aachen (DE); Andre Chuev, Aachen (DE); Qing Tan, Danvers, MA (US); Samuel Brown, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 319 days.

(21) Appl. No.: 18/120,018

(22) Filed: Mar. 10, 2023

(65) Prior Publication Data

US 2023/0285740 A1 Sep. 14, 2023

Related U.S. Application Data

(60) Provisional application No. 63/318,593, filed on Mar. 10, 2022.

(51) Int. Cl.
*A61M 60/538* (2021.01)
*A61M 60/178* (2021.01)
(Continued)

(52) U.S. Cl.
CPC ........ *A61M 60/538* (2021.01); *A61M 60/178* (2021.01); *A61M 60/216* (2021.01);
(Continued)

(58) Field of Classification Search
CPC .............. A61M 60/538; A61M 60/178; A61M 60/216; A61M 60/422; A61M 60/546;
(Continued)

(56) References Cited

U.S. PATENT DOCUMENTS

| | | | |
|---|---|---|---|
| 6,142,752 A | 11/2000 | Akamatsu et al. | |
| 2004/0064012 A1* | 4/2004 | Yanai .................. | A61M 60/546 600/16 |

(Continued)

FOREIGN PATENT DOCUMENTS

| | | | | |
|---|---|---|---|---|
| JP | 2017522929 A | * | 8/2017 | .............. A61M 1/28 |

OTHER PUBLICATIONS

International Search Report and Written Opinion from the International Searching Authority for International Application No. PCT/US2023/014717 dated Jun. 13, 2023.

*Primary Examiner* — Benjamin R Schmitt
(74) *Attorney, Agent, or Firm* — Pierce Atwood LLP

(57) ABSTRACT

Methods and apparatus for determining flow through a circulatory support device are provided. The method comprises receiving a motor current signal from a motor of the circulatory support device, determining within a time window of the motor current signal, a measured current value at which flow through the circulatory support device is maximum, determining an offset value based, at least in part, on the measured current value, determining based, at least in part, on the received motor current signal, whether an abnormal condition has occurred, adjusting the motor current signal based, at least in part, on the offset value and the determination of whether an abnormal condition has occurred to produce an adjusted motor current signal, and determining the flow through the circulatory support device based, at least in part, on the adjusted motor current signal.

20 Claims, 15 Drawing Sheets

(51) Int. Cl.

| | |
|---|---|
| *A61M 60/216* | (2021.01) |
| *A61M 60/422* | (2021.01) |
| *A61M 60/546* | (2021.01) |
| *F04B 51/00* | (2006.01) |
| *G01F 11/00* | (2006.01) |
| *G01F 25/10* | (2022.01) |

(52) U.S. Cl.
CPC ........ *A61M 60/422* (2021.01); *A61M 60/546* (2021.01); *F04B 51/00* (2013.01); *G01F 11/006* (2013.01); *G01F 25/10* (2022.01); *Y02B 30/70* (2013.01)

(58) Field of Classification Search
CPC ........ G01F 11/006; G01F 25/10; F04B 51/00; Y02B 30/70
See application file for complete search history.

(56) References Cited

U.S. PATENT DOCUMENTS

| | | | |
|---|---|---|---|
| 2012/0245681 A1 | 9/2012 | Casas et al. | |
| 2013/0030240 A1* | 1/2013 | Schima | .............. A61M 60/546 |
| | | | 600/16 |
| 2016/0058929 A1 | 3/2016 | Medvedev et al. | |
| 2019/0351116 A1 | 11/2019 | Kudlik | |
| 2020/0289730 A1* | 9/2020 | Brown | ................ A61M 60/178 |

* cited by examiner

340

DETERMINE SPEED OF MOTOR ⎯ 610

DETERMINE EXPECTED MOTOR CURRENT VALUE ASSOCIATED WITH MAXIMUM FLOW AT SPEED OF MOTOR ⎯ 620

DETERMINE OFFSET VALUE AS DIFFERENCE BETWEEN EXPECTED MOTOR CURRENT VALUE AND MEASURED MOTOR CURRENT VALUE ⎯ 630

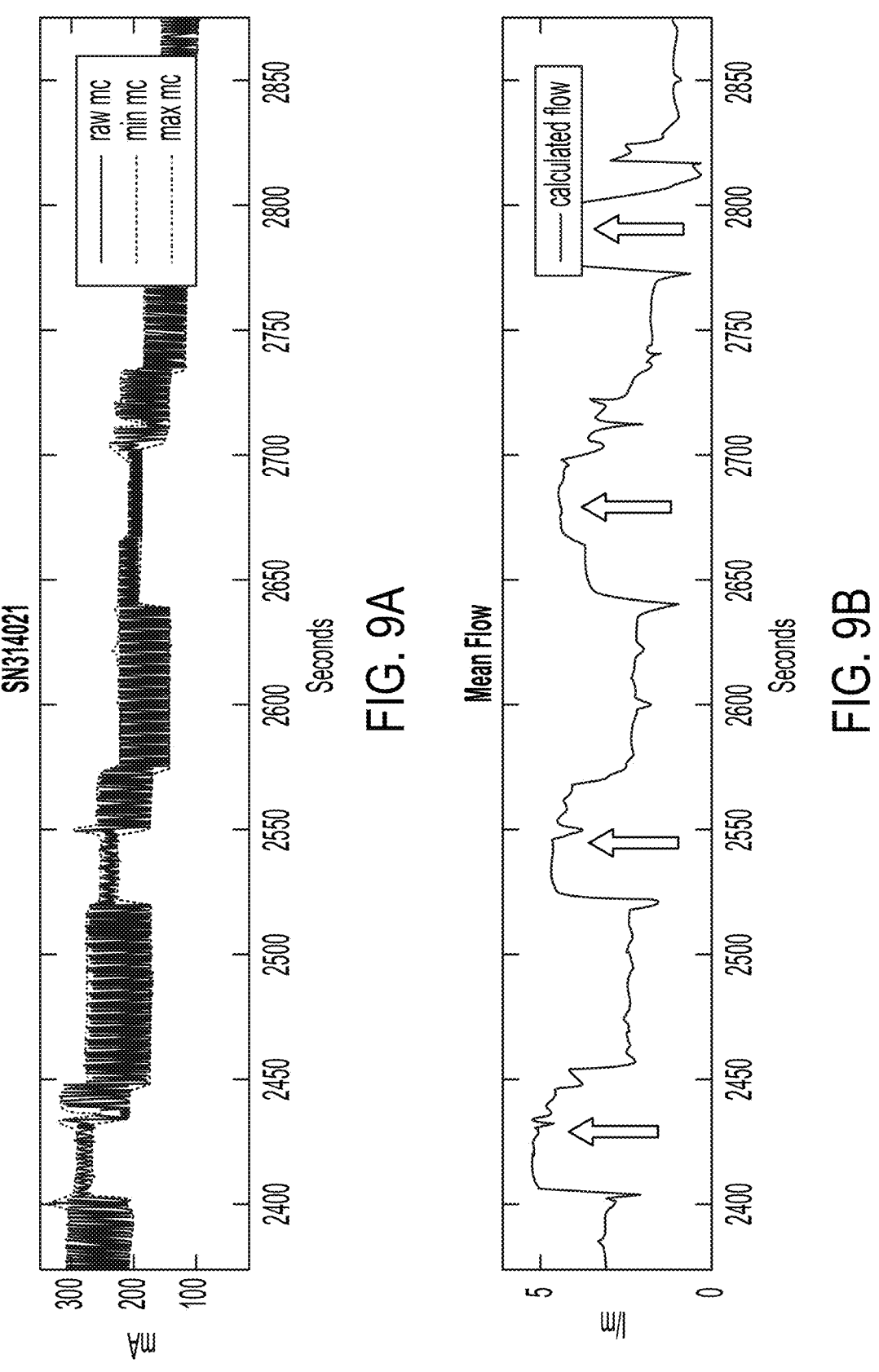

ADAPTIVE FLOW CALCULATION FOR A MECHANICAL CIRCULATORY SUPPORT DEVICE

RELATED APPLICATIONS

This application claims the benefit under 35 U.S.C. § 119(e) of U.S. Provisional Patent Application Ser. No. 63/318,593, filed Mar. 10, 2022, and entitled, "ADAPTIVE FLOW CALCULATION FOR A MECHANICAL CIRCULATORY SUPPORT DEVICE," the entire contents of which is incorporated herein by reference.

TECHNICAL FIELD

The subject application relates to adaptive flow calculation, in particular to adaptive flow calculation for a mechanical circulatory support device.

BACKGROUND

Fluid pumps, such as blood pumps, are used in the medical field in a wide range of applications and purposes. An intravascular blood pump is a pump that can be advanced through a patient's vasculature, i.e., veins and/or arteries, to a position in the patient's heart or elsewhere within the patient's circulatory system. For example, an intravascular blood pump may be inserted via a catheter and positioned to span a heart valve. The intravascular blood pump is typically disposed at the end of the catheter. Once in position, the pump may be used to assist the heart and pump blood through the circulatory system and, therefore, temporarily reduce workload on the patient's heart, such as to enable the heart to recover after a heart attack. An exemplary intravascular blood pump is available from ABIOMED, Inc., Danvers, MA under the tradename Impella® heart pump.

Such pumps can be positioned, for example, in a cardiac chamber, such as the left ventricle, to assist the heart. In this case, the blood pump may be inserted via a femoral artery by means of a hollow catheter and introduced up to and into the left ventricle of a patient's heart. From this position, the blood pump inlet draws in blood and the blood pump outlet expels the blood into the aorta. In this manner, the heart's function may be replaced or at least assisted by operation of the pump.

An intravascular blood pump is typically connected to a respective external heart pump controller that controls the heart pump, such as motor speed, and collects and displays operational data about the blood pump, such as heart signal level, battery temperature, blood flow rate and plumbing integrity. An exemplary heart pump controller is available from Abiomed, Inc. under the trade name Automated Impella Controller®. The controller raises alarms when operational data values fall beyond predetermined values or ranges, for example if a leak, suction, and/or pump malfunction is detected. The controller may include a video display screen upon which is displayed a graphical user interface configured to display the operational data and/or alarms.

SUMMARY

Described herein are systems and methods for calculating flow through a mechanical circulatory device.

In some embodiments of the present technology a method of determining flow through a circulatory support device is provided. The method comprises receiving a motor current signal from a motor of the circulatory support device, determining within a time window of the motor current signal, a measured current value at which flow through the circulatory support device is maximum, determining an offset value based, at least in part, on the measured current value, determining based, at least in part, on the received motor current signal, whether an abnormal condition has occurred, adjusting the motor current signal based, at least in part, on the offset value and the determination of whether an abnormal condition has occurred to produce an adjusted motor current signal, and determining the flow through the circulatory support device based, at least in part, on the adjusted motor current signal.

In one aspect, the measured current value is a maximum current value or a minimum current value within the time window.

In one aspect, the measured current value is the minimum current value within the time window.

In one aspect, a length of the time window is between one and four seconds.

In one aspect, the length of the time window is two seconds.

In one aspect, determining the offset value is further based, at least in part, on a speed of the motor.

In one aspect, the method further comprises storing, on at least one storage device, data relating flow values to motor current values for each of a plurality of motor speeds, and determining the offset value comprises determining based, at least in part, on the stored data, an expected current value associated with a maximum flow at the speed of the motor, and determining the offset value as a difference between the current value and the expected current value.

In one aspect, adjusting the motor current signal comprises adding the offset value to the motor current signal to produce the adjusted motor current signal.

In one aspect, determining the flow through the circulatory support device comprises determining the flow further based, at least in part, on the stored data relating flow values to motor current values at the speed of the motor.

In one aspect, adjusting the motor current signal based, at least in part, on the offset value and the determination of whether an abnormal condition has occurred to produce an adjusted motor current signal comprises using an offset value of zero when it is determined that an abnormal condition has occurred.

In one aspect, determining whether an abnormal condition has occurred comprises determining whether the circulatory support device is in a suction state or a decoupling state.

In one aspect, the method further comprises storing previously determined offset values in a buffer, and storing the determined offset value in the buffer.

In one aspect, each of the previously determined offset values in the buffer is a scaled offset value scaled based on a speed of the motor at the time when the offset value was determined, and storing the determined offset value in the buffer comprises scaling the determined offset value based on the speed of the motor, and storing the scaled determined offset value in the buffer.

In one aspect, adjusting the motor current signal comprises adjusting the motor current signal based, at least in part, on a median value of the previously determined offset values in the buffer.

In one aspect, adjusting the motor current signal comprises transforming the median value based on a present speed of the motor, and adjusting the motor current signal based on the transformed median value.

In one aspect, the method further comprises storing the determined offset value in the buffer only when it is determined that an abnormal condition has not occurred.

In one aspect, the method further comprises filtering the received motor current signal, and adjusting the motor current signal comprises adjusting the filtered motor current signal.

In one aspect, the method further comprises displaying on at least one graphical user interface, an indication of the determined flow through the circulatory support device.

In some embodiments of the present technology, a circulatory support device is provided. The circulatory support device comprises a rotor, a motor configured to drive rotation of the rotor at one or more speeds, and at least one controller. The at least one controller is configured to receive a motor current signal from the motor, determine within a time window of the motor current signal, a measured current value at which flow through the circulatory support device is maximum, determine an offset value based, at least in part, on the measured current value, determine based, at least in part, on the received motor current signal, whether an abnormal condition has occurred, adjust the motor current signal based, at least in part, on the offset value and the determination of whether an abnormal condition has occurred to produce an adjusted motor current signal, and determine the flow through the circulatory support device based, at least in part, on the adjusted motor current signal.

In one aspect, the measured current value is a maximum current value or a minimum current value within the time window.

In one aspect, the measured current value is the minimum current value within the time window.

In one aspect, a length of the time window is between one and four seconds.

In one aspect, the length of the time window is two seconds.

In one aspect, determining the offset value is further based, at least in part, on a speed of the motor.

In one aspect, the at least one controller is further configured to store, on at least one storage device, data relating flow values to motor current values for each of a plurality of motor speeds, and determining the offset value comprises determining based, at least in part, on the stored data, an expected current value associated with a maximum flow at the speed of the motor, and determining the offset value as a difference between the current value and the expected current value.

In one aspect, adjusting the motor current signal comprises adding the offset value to the motor current signal to produce the adjusted motor current signal.

In one aspect, determining the flow through the circulatory support device comprises determining the flow further based, at least in part, on the stored data relating flow values to motor current values at the speed of the motor.

In one aspect, adjusting the motor current signal based, at least in part, on the offset value and the determination of whether an abnormal condition has occurred to produce an adjusted motor current signal comprises using an offset value of zero when it is determined that an abnormal condition has occurred.

In one aspect, determining whether an abnormal condition has occurred comprises determining whether the circulatory support device is in a suction state or a decoupling state.

In one aspect, the at least one controller is further configured to store previously determined offset values in a buffer, and store the determined offset value in the buffer.

In one aspect, each of the previously determined offset values in the buffer is a scaled offset value scaled based on a speed of the motor at the time when the offset value was determined, and storing the determined offset value in the buffer comprises scaling the determined offset value based on the speed of the motor, and storing the scaled determined offset value in the buffer.

In one aspect, adjusting the motor current signal comprises adjusting the motor current signal based, at least in part, on a median value of the previously determined offset values in the buffer.

In one aspect, adjusting the motor current signal comprises transforming the median value based on a present speed of the motor, and adjusting the motor current signal based on the transformed median value.

In one aspect, the at least one controller is further configured to store the determined offset value in the buffer only when it is determined that an abnormal condition has not occurred.

In one aspect, the at least one controller is further configured to filter the received motor current signal, and adjusting the motor current signal comprises adjusting the filtered motor current signal.

In one aspect, the least one controller is further configured to display on at least one graphical user interface, an indication of the determined flow through the circulatory support device.

In some embodiments of the present technology a controller for a circulatory support device is provided. The controller comprises at least one hardware processor configured to receive a motor current signal from a motor of the circulatory support device, determine within a time window of the motor current signal, a measured current value at which flow through the circulatory support device is maximum, determine an offset value based, at least in part, on the measured current value, determine based, at least in part, on the received motor current signal, whether an abnormal condition has occurred, adjust the motor current signal based, at least in part, on the offset value and the determination of whether an abnormal condition has occurred to produce an adjusted motor current signal, and determine the flow through the circulatory support device based, at least in part, on the adjusted motor current signal.

In one aspect, the measured current value is a maximum current value or a minimum current value within the time window.

In one aspect, the measured current value is the minimum current value within the time window.

In one aspect, a length of the time window is between one and four seconds.

In one aspect, the length of the time window is two seconds.

In one aspect, determining the offset value is further based, at least in part, on a speed of the motor.

In one aspect, the at least one hardware processor is further configured to store, on at least one storage device, data relating flow values to motor current values for each of a plurality of motor speeds, and determining the offset value comprises determining based, at least in part, on the stored data, an expected current value associated with a maximum flow at the speed of the motor, and determining the offset value as a difference between the current value and the expected current value.

In one aspect, adjusting the motor current signal comprises adding the offset value to the motor current signal to produce the adjusted motor current signal.

In one aspect, determining the flow through the circulatory support device comprises determining the flow further based, at least in part, on the stored data relating flow values to motor current values at the speed of the motor.

In one aspect, adjusting the motor current signal based, at least in part, on the offset value and the determination of whether an abnormal condition has occurred to produce an adjusted motor current signal comprises using an offset value of zero when it is determined that an abnormal condition has occurred.

In one aspect, determining whether an abnormal condition has occurred comprises determining whether the circulatory support device is in a suction state or a decoupling state.

In one aspect, the at least one hardware processor is further configured to store previously determined offset values in a buffer, and store the determined offset value in the buffer.

In one aspect, each of the previously determined offset values in the buffer is a scaled offset value scaled based on a speed of the motor at the time when the offset value was determined, and storing the determined offset value in the buffer comprises scaling the determined offset value based on the speed of the motor, and storing the scaled determined offset value in the buffer.

In one aspect, adjusting the motor current signal comprises adjusting the motor current signal based, at least in part, on a median value of the previously determined offset values in the buffer.

In one aspect, adjusting the motor current signal comprises transforming the median value based on a present speed of the motor, and adjusting the motor current signal based on the transformed median value.

In one aspect, the at least one hardware processor is further configured to store the determined offset value in the buffer only when it is determined that an abnormal condition has not occurred.

In one aspect, the at least one hardware processor is further configured to filter the received motor current signal, and adjusting the motor current signal comprises adjusting the filtered motor current signal.

In one aspect, the least one hardware processor is further configured to display on at least one graphical user interface, an indication of the determined flow through the circulatory support device.

BRIEF DESCRIPTION OF DRAWINGS

FIGS. 9A-9C illustrate flow calculation when motor current adjustment remains active despite an abnormal condition being detected.

DETAILED DESCRIPTION

Traditionally, blood flow through a mechanical circulatory support device, such as a catheter-based heart pump inserted into a ventricle of the patient, is calculated based on motor speed and motor current sensed from the pump motor. For instance, data characterizing the relationship between flow and motor current (also referred to herein as Q vs. MC curves) for each of a plurality of motor speeds may be stored, and the stored data and a measured motor current value may be used to estimate the flow when the pump motor is operated at a particular speed. In some intravascular heart pump systems, the pump motor is located inside of the patient near the pump. For instance, once placed in the patient, the pump may be located in the left ventricle and the pump motor may be located across the aortic valve in the aorta. In such a configuration, the sensed motor current may be considered stable enough to accurately estimate flow using the technique described above. Some pump systems may locate the pump motor outside of the patient (and thus necessarily at a distance from the pump) to decrease the maximum outer diameter of the pump when inserted and removed from the patient. In such a configuration, the sensed motor current may not be stable enough over time to accurately calculate flow through the pump. As described in more detail below, some embodiments of the present technology account for the instability of sensed motor current in such configurations by making continuous or near-continuous adjustments (e.g., to the motor current signal) during the flow calculation process.

Figures 1A, 1B:
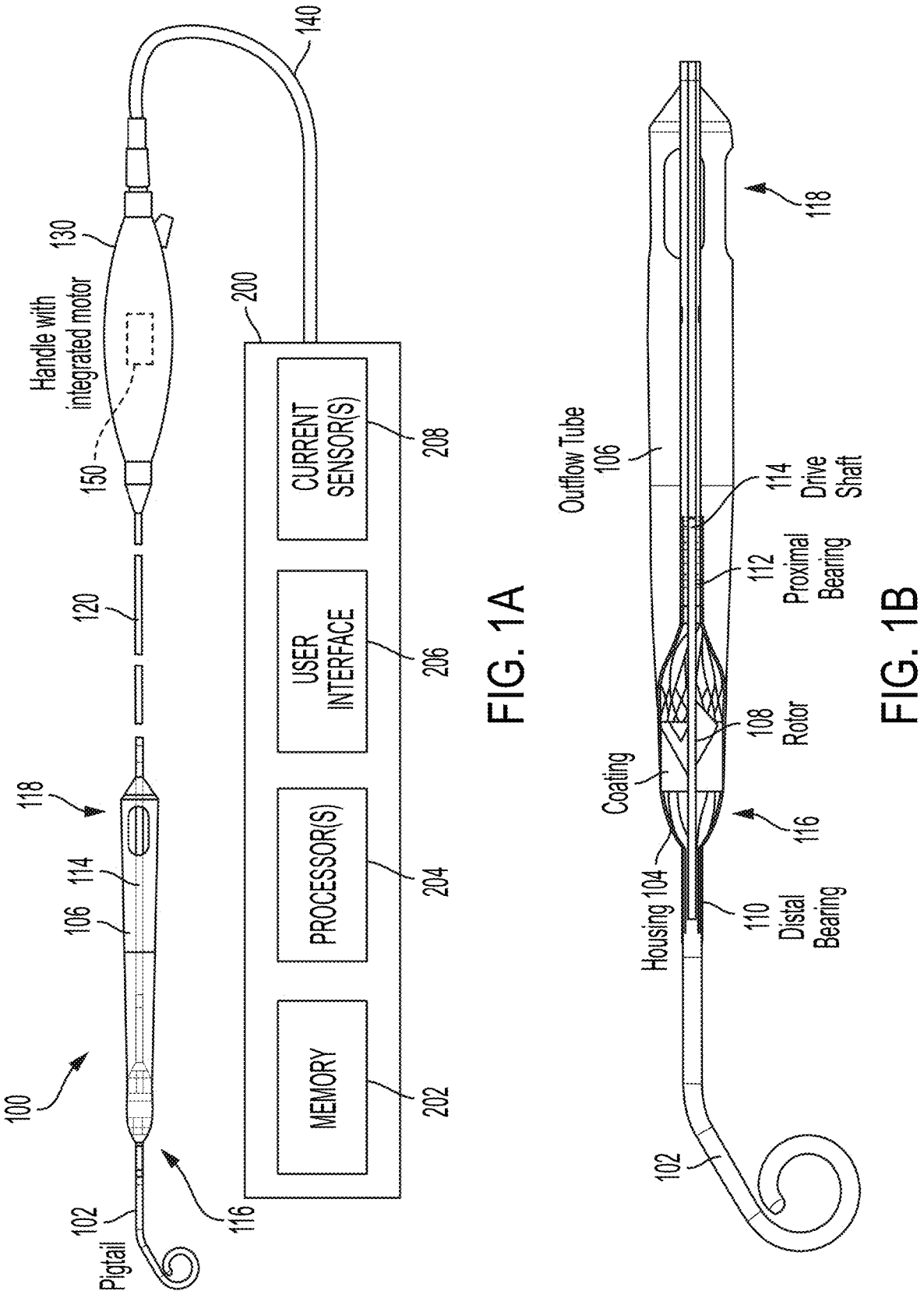
FIG. 1A illustrates a pump system in accordance with some embodiments of the present technology.
FIG. 1B is a cross-sectional view of a portion of the pump system of FIG. 1A.

A pump system 100 for use with some embodiments of the present technology is shown in FIGS. 1A and 1B. As shown, pump system 100 is coupled to a control unit 200. Pump 100 includes a distal atraumatic tip 102, a pump housing 104 surrounding a rotor 108, an outflow tube 106, distal bearing 110, proximal bearing 112, inlet 116, outlet 118, catheter 120, handle 130, cable 140, and motor 150. Pump housing 104 may be configured as a frame structure formed by a mesh with openings which may, at least in part, be covered by an elastic material. A proximal portion of pump housing 104 extends into and is mounted in the hollow interior of outflow tube 106, and a distal portion of pump housing 104 extends distally beyond the distal end of outflow tube 106. The exposed openings in the pump housing 104 extending distally beyond outflow tube 106 form the inlet 116 of pump 100. The proximal end of outflow tube 106 includes a plurality of openings that form the outlet 118 of pump 100. Rotor 108 is rotationally mounted between distal bearing 110 and proximal bearing 112, and is coupled to a distal end of drive shaft 114. Drive shaft 114 is flexible and extends through catheter 120, through the hollow interior of outflow tube 106, into handle 130 and is coupled to motor 150, which is housed in handle 130. The proximal end of handle 130 is coupled via cable 140 to control unit 200. A fluid may be circulated through the catheter 120 proximate to the drive shaft 114 and in the space surrounding the distal bearing 110 and proximal bearing 112 to lubricate those components and reduce friction during operation of the pump 100.

Control unit 200 includes one or more memory 202, one or more processors 204, user interface 206, and one or more current sensors 208. Processor(s) 204 may comprise one or more microcontrollers, one or more microprocessors, one or more application specific integrated circuits (ASICs), one or more digital signal processors, program memory, or other computing components. Processor(s) 204 is communicatively coupled to the other components (e.g., memory 202, user interface 206, current sensor(s) 208) of control unit 200 and is configured to control one or more operations of pump 100. As a non-limiting example, control unit 200 may be implemented as an Automated Impella Controller® from Abiomed, Inc., Danvers, MA In some aspects, memory 202 is included as a portion of processor(s) 204 rather than being provided as a separate component.

During operation, processor(s) 204 is configured to control the electrical power delivered to motor 150 (e.g., by controlling a power supply (not shown)) by a power supply line (not shown) in cable 140, thereby controlling the speed of the motor 150. Current sensor(s) 208 may be configured to sense motor current associated with an operating state of the motor 150, and processor(s) 204 may be configured to receive the output of current sensor(s) 208 as a motor current signal. Processor(s) 204 may further be configured to determine a flow through the pump 100 based, at least in part, on the motor current signal and the motor speed, as described in more detail below. Current sensor(s) 208 may be included in control unit 200 or may be located along any portion of the power supply line in cable 140. Additionally or alternatively, current sensor(s) 208 may be included in motor 150 and processor(s) 204 may be configured to receive the motor current signal via a data line (not shown) in cable 140 coupled to processor(s) 204 and motor 150.

Memory 202 may be configured to store computer-readable instructions and other information for various functions of the components of control unit 200. In one aspect, memory 202 includes volatile and/or non-volatile memory, such as, an electrically erasable programmable read-only memory (EEPROM).

User interface 206 may be configured to receive user input via one or more buttons, switches, knobs, etc. Additionally, user interface 206 may include a display configured to display information and one or more indicators, such as light indicators, audio indicators, etc., for conveying information and/or providing alerts regarding the operation of pump 100.

Pump 100 is designed to be insertable into a patient's body, e.g., into a left ventricle of the heart, with an introducer system. In one aspect, housing 104, rotor 108, and outflow tube 106 are radially compressible to enable pump 100 to achieve a relatively small outer diameter of, for example, 9 Fr (3 mm) during insertion. When pump 100 is inserted into the patient, e.g., into a left ventricle, handle 130 and motor 150 remain disposed outside the patient. During operation, motor 150 is controlled by processor(s) 204 to drive rotation of drive shaft 114 and rotor 108 to convey blood from inlet 116 to outlet 118. It is to be appreciated that rotor 108 may be rotated by motor 150 in reverse to convey blood in the opposite direction (in this case, the openings of 118 form the inlet and the openings of 116 form the outlet). In one aspect, pump 100 is intended to be used during high-risk procedures for a duration of up to six hours, though it should be understood that the technology described herein is not limited to any particular types of procedures and/or use durations.

Figure 2:
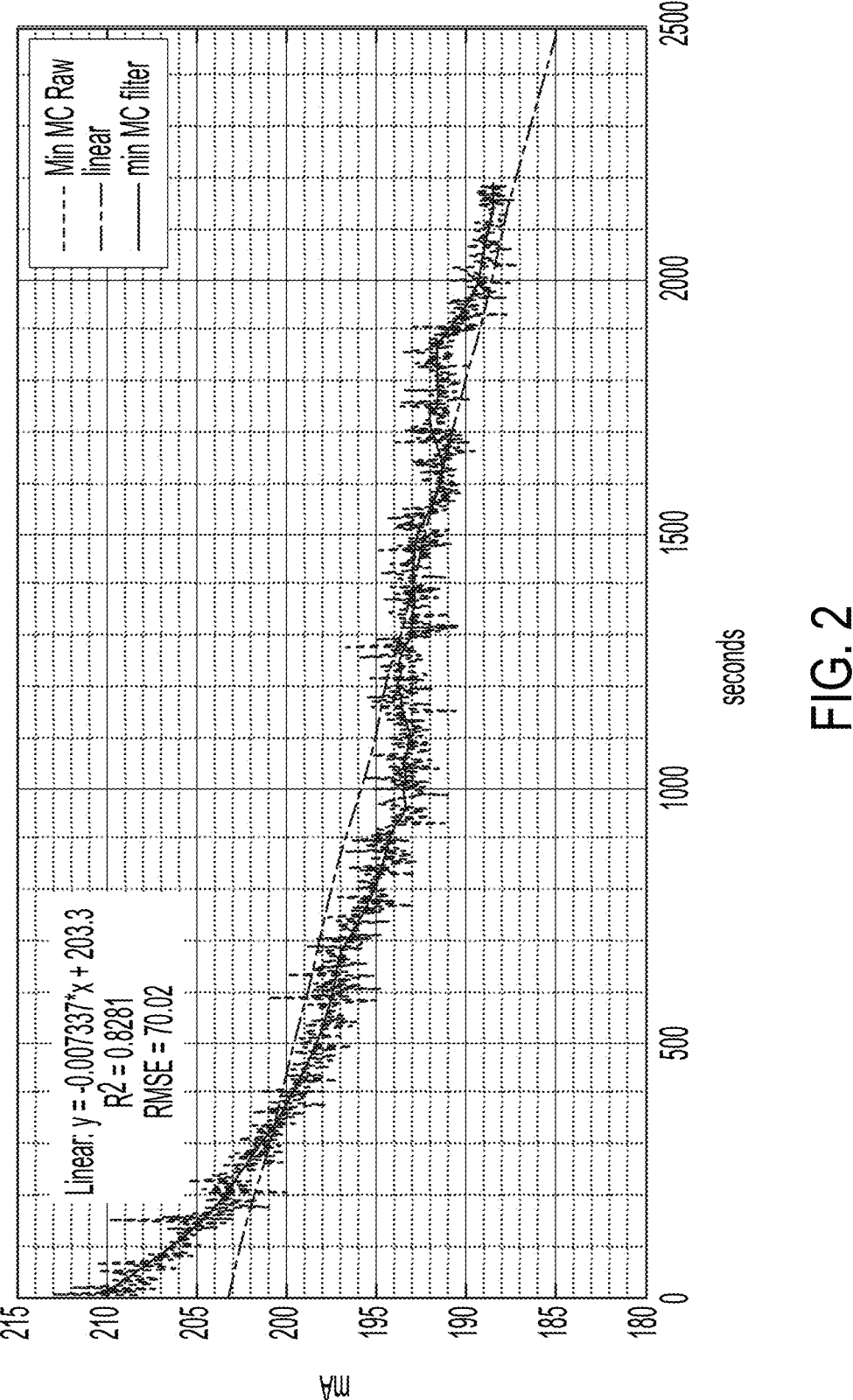
FIG. 2 is a diagram illustrating changes over time in the measured minimum motor current of a pump system.

Because the motor 150 of pump 100 drives rotation of rotor 108 via a flexible drive shaft 114 disposed in catheter 120, the motor current sensed by current sensor(s) 204 is not stable, but instead changes over time, especially within an initial period after placement of the pump in the heart of the patient (e.g., within the first thirty minutes after placement). The instability of the sensed motor current signal may be caused by, among other things, changes in characteristics (e.g., a decrease in friction) associated with rotation of the flexible drive shaft 114, as viscosity of the lubricating fluid also changes during operation. FIG. 2 illustrates an example of how the minimum motor current determined from a portion of the motor current signal decreases over time during operation of pump 100. In the graph of FIG. 2, the y-axis represents minimum motor current (in mA) determined during a two second time window of the sensed motor current signal and the x-axis represents time. The inventors have recognized and appreciated that prior flow calculation techniques or algorithms that assume a stable motor current signal cannot be used to accurately calculate flow through pump 100 in which the motor current changes over time. To this end, some embodiments of the present technology account for changes in the motor current signal sensed from pump 100 by adaptively updating the motor current signal prior to calculating flow based on that signal.

The flow calculation techniques described herein may be implemented in control unit 200 of pump system 100. For example, computer-readable instructions for one or all of the techniques described herein may be stored in the memory 202 and executed by the one or more processors 204 of control unit 200 during use of the pump 100. Moreover, the parameters and settings of the one or more processors used in the techniques described herein, such as predetermined thresholds, predetermined window lengths, and/or any other parameters and settings of the techniques described herein may be stored in memory 202.

Figure 3:
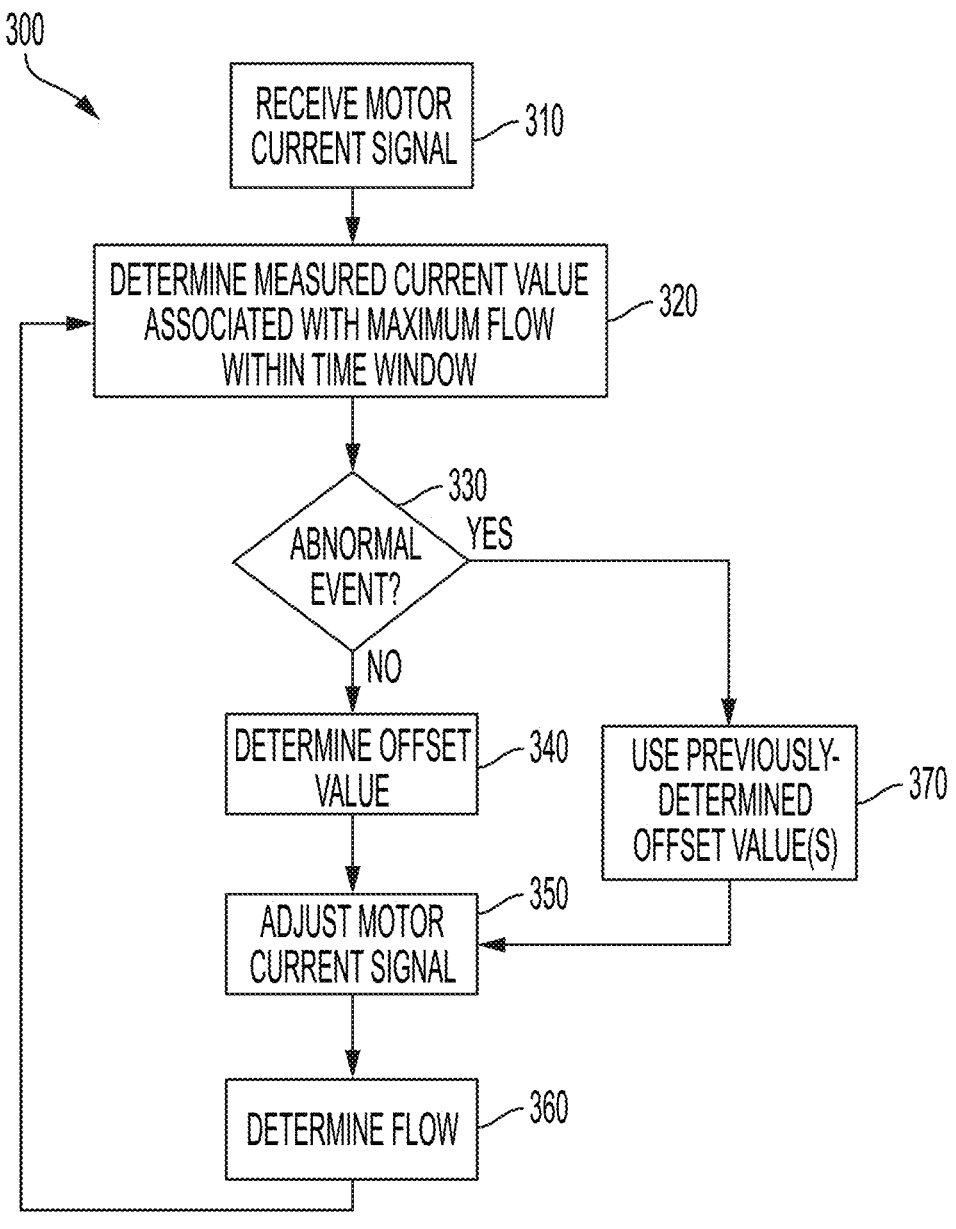
FIG. 3 is a flowchart of a process for adapting a motor current signal used to determine flow through a pump system in accordance with some embodiments of the present technology.

FIG. 3 is a flowchart of a process 300 for determining flow through a mechanical circulatory support device (e.g., pump 100) based, at least in part, on a motor current signal associated with a motor of the device, in accordance with some embodiments of the present technology. In act 310, a motor current signal is received, for example from one or more motor current sensors 208, as described above in connection with FIG. 1A. Process 300 then proceeds to act 320, where a time window of predetermined length (e.g., between 1 and 4 seconds) of the motor current signal is analyzed. In some embodiments, the predetermined length of the time window is 2 seconds. It is to be appreciated that other time durations less than or greater than 2 seconds (e.g., 1 second, 5 seconds, etc.) may be used for the predetermined length of the time window in act 320.

Within the time window, a motor current value associated with maximum flow through the pump is determined. Flow though the pump is based on the pressure difference between the inlet and outlet of the pump through which blood is conveyed when the pump is in operation. During systole, the pressure difference between the inlet and outlet of the pump is zero, resulting in the maximum flow through the pump. Depending on the pump design, the minimum motor current value during the time window may correspond to the maximum flow (at systole) or the maximum motor current value during the time window may correspond to the maximum flow (at systole). Accordingly, the techniques described herein may be configured to determine the minimum motor current value or the maximum motor current value in the time window depending on the type of pump design.

Process 300 then proceeds to act 330, where it is determined whether an abnormal event has occurred. Continuously or near continuously adjusting the motor current during operation of the pump may provide for a reliable calculation of flow under normal operating conditions. However, the inventors have recognized and appreciated that continuing to adjust the motor current when the pump is not operating normally may result in an incorrect flow calculation. Accordingly, in some embodiments, the presence of "abnormal events" during operation of the pump are detected and the adaptation of the motor current using the techniques described herein is modified (e.g., suspended) during occurrence of the abnormal event. Abnormal events may include, but are not limited to, suction events in which the inlet of the pump is obstructed with cardiac tissue or other material thereby obstructing flow through the pump, and decoupling events which may occur prior to suction events. Non-limiting examples of techniques for detecting suction and decoupling events are described in more detail below. Abnormal events other than suction events and decoupling events may also be detected and motor current adaptation suspended in response to the detection, as embodiments of the present technology are not limited in this respect.

If it is determined in act 330 that an abnormal event has not been detected (e.g., the pump is operating under normal conditions), process 300 proceeds to act 340 where an offset value is determined. An exemplary technique for determining an offset value in accordance with some embodiments is described below in connection with the flowchart of FIG. 6. After determination of the offset value, process 300 proceeds to act 350, where the measured motor current signal is adjusted based, at least in part, on the offset value determined in act 340. Process 300 then proceeds to act 360, where flow through the pump is determined, at least in part, on the adjusted motor current signal. An illustrative example of determining flow through the pump based on a motor current signal is discussed in further detail below with respect to FIGS. 4 and 5. Process 300 then returns to act 320 where a measured current value associated with maximum flow within a new time window (e.g., a next 2 second time window) is determined, and acts 320 through 360 may be repeated thereby adapting the motor current signal in a "continuous" manner until flow calculation is no longer desired.

As discussed above, the inventors have recognized and appreciated that when the pump is not operating normally (e.g., when an abnormal event is detected in act 330 of process 300), the technique of continuously adapting the motor current signal based on a calculated offset value as discussed above in connection with acts 340 and 350 may result in an incorrect flow determination in act 360. Accordingly, when an abnormal event is detected in act 330, process 300 proceeds to act 370, where one or more previously-determined offset values are used to adjust the measured motor current signal in act 350. For instance, each time that an offset value is determined in act 340, the determined offset value may be stored in memory (e.g., memory 202). Upon detection of an abnormal event, the previously-determined offset value stored in memory may be used to adjust the motor current signal. In this way, the continuous adjustment of motor current is suspended while the abnormal event continues to be detected in act 330, and the same previously-determined offset value is used to adjust the motor current signal during each new time window.

In some embodiments, rather than storing a single previously-determined offset value in memory, a plurality of determined offset values are stored in a buffer in memory and the offset value used to adjust the motor current signal during an abnormal event is based on a plurality of offset values stored in the buffer. For instance, the buffer may store the five most recent determined offset values, and a median of the five offset values stored in the buffer may be used to adjust the motor current signal during the abnormal event. Other statistical metrics other than the median value of the values in the buffer including, but not limited to, the mean of the stored values or a weighted average of the stored values may alternatively be used. It should be appreciated that the buffer may store any suitable number of values, and storing five values is merely one possibility. For instance, the buffer may be configured to store two values, three values, ten values or more than ten values. By storing a plurality of offset values in a buffer and selecting an offset value based on the plurality of stored offset values, the motor current adaptation exhibits hysteresis to enable a transition of motor current adjustments to be smoother than if only a single previously-determined offset value was stored and used in act 370. In some embodiments, offset values are only added to the buffer when an abnormal value is not detected in act 330 (e.g., during normal operation of the pump). In this way the offset values in the buffer remain static during the course of the abnormal event.

Figures 4A, 4B, 4C:
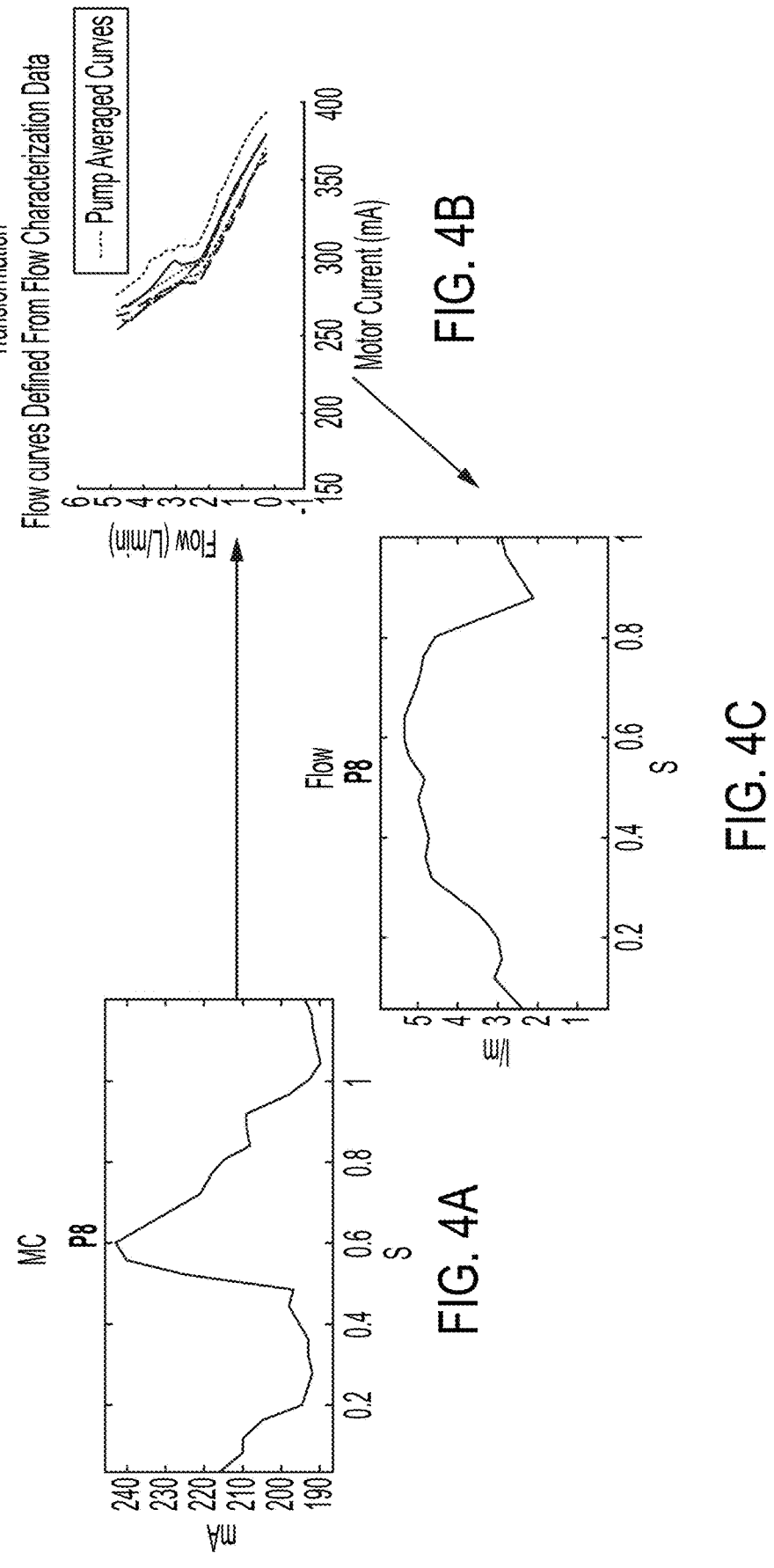
FIGS. 4A-4C schematically illustrate a process for determining flow based on sensed motor current in accordance with some embodiments of the present technology.

FIGS. 4A-4C schematically illustrate a technique for calculating flow based on a motor current signal within a time window in accordance with some embodiments. FIG. 4A illustrates a motor current (MC) signal during a single cardiac cycle with motor current in milliamps (mA) being represented on the y-axis and time being represented on the x-axis. Based on the value of the motor current signal, the corresponding flow through the pump may then be calculated using a stored relationship (also referred to herein as "flow curves" or "Q vs. MC curves") that relates flow values through the pump and motor current, an example of which is illustrated in FIG. 4B, with flow being represented on the y-axis and motor current being represented on the x-axis. For instance, values represented graphically as a flow curve may be stored in memory as a lookup table that is used to associate motor current values with flow values at a particular motor speed.

The flow curves at different motor speeds may be determined during an "offline" testing procedure that approximates normal operation of the device in a patient. During the testing procedure, flow and motor current are measured at different motor speeds, and a plurality of flow curves, one for each motor speed, are determined based on the measured data. FIG. 4B shows multiple flow curves determined for a plurality of pumps tested at the same motor speed. An average flow curve across the plurality of tested pumps may be stored and used to calculate flow during operation of the pump.

Figure 5:
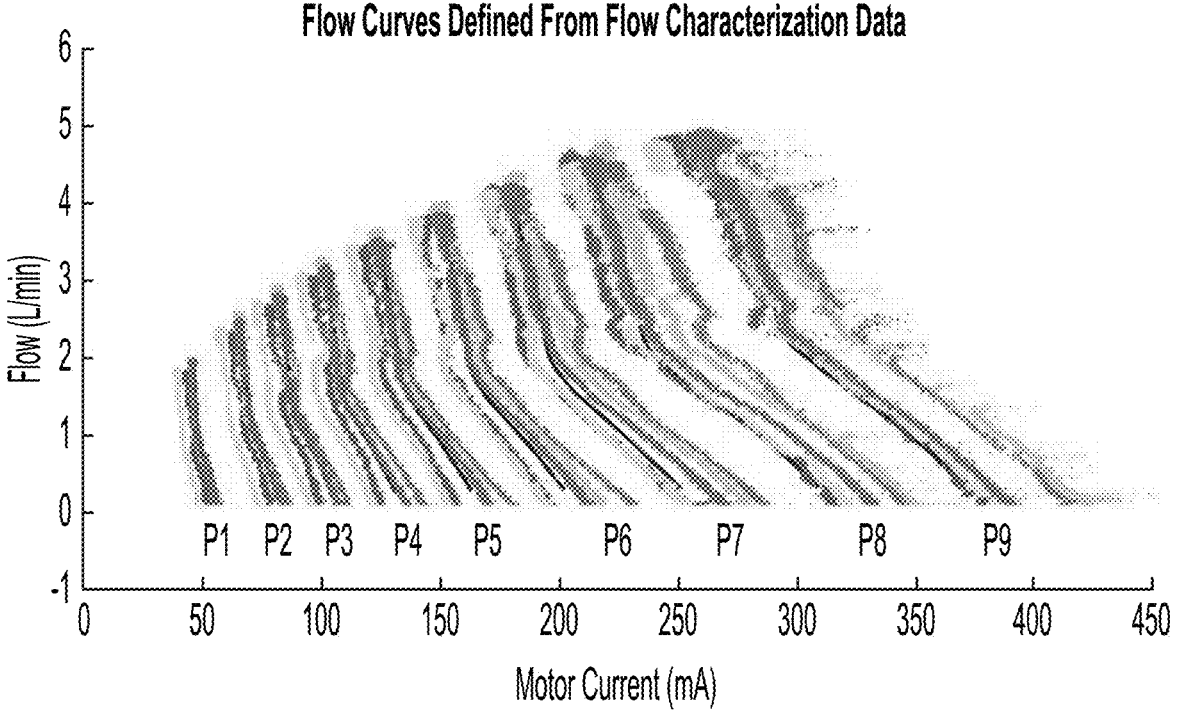
FIG. 5 illustrates a plurality of flow curves at different motor speeds, wherein the flow curves describe a relationship between flow through a pump system and motor current.

FIG. 5 shows a plurality of flow curves at different motor speeds, labeled in FIG. 5 as P1 through P9, with P1 being the slowest speed and P9 being the fastest speed of the motor. Similar to the plot in FIG. 4B which illustrated measurements at a single motor speed, in the plot of FIG. 5, multiple flow curves are also shown at each of the motor speeds P1-P9. For each of the motor speeds, values corresponding to a single flow curve (e.g., as an average of the flow curves shown) may be stored as a lookup table that may be used to calculate flow during operation of a pump.

Figure 6:
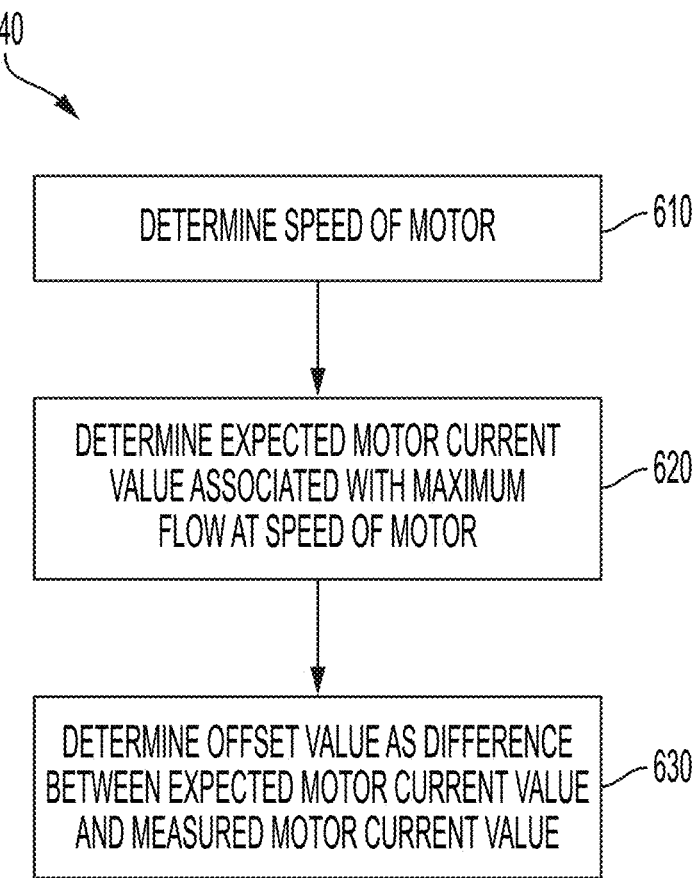
FIG. 6 is a flowchart of a process for determining an offset value used to adjust a measured motor current value in accordance with some embodiments of the present technology.

FIG. 6 illustrates an example implementation of process 340 for determining an offset value to use for adaptively adjusting a motor current signal of a pump in accordance with some embodiments. In act 610, the current motor speed is determined. The current motor speed may be determined in any suitable way. For instance, the motor may be configured to operate at one of a plurality of fixed speeds (e.g., designated as P1 to P9), and the current motor speed may be determined as the fixed speed at which the motor is currently set to operate. The process then proceeds to act 620 where the expected motor current value associated with maximum flow through the pump at the current speed of the motor is determined. As discussed above in connection with FIG. 5, some embodiments store data that describe relationships between flow through the pump and motor current at each of plurality of fixed motor speeds, also referred to herein as flow curves. The uppermost point along the y-axis of each of these flow curves represents the expected maximum flow and corresponding expected motor current associated with that maximum flow when the motor is operating at the particular motor speed associated with the flow curve. Accordingly, by knowing the current speed of the motor, the expected motor current value associated with maximum flow at the current motor speed can be determined by referencing the flow curve data associated with the motor speed.

The process of FIG. 6 then proceeds to act 630 where the offset value is determined based on a comparison of the expected motor current value when flow is maximum determined in act 620 and the measured or "actual" motor current value determined within the particular time analysis window of the motor current signal.

As discussed above, the flow through the pump is maximum during a cardiac cycle during systole because the pressure difference between the inlet and outlet of the pump at that time is at a minimum (e.g., zero). For pump designs in which the minimum motor current value corresponds to the maximum flow, the minimum motor current value within the analysis time window is determined as the measured motor current value used in the comparison of act 630 of the process of FIG. 6. In the example of FIG. 4A, the minimum motor current value occurs shortly after 1 s during the time window. The difference between the measured minimum motor current value and the motor current value associated with the uppermost point in the relevant flow curve (i.e., the expected motor current value at maximum flow for the current motor speed) is used to determine the offset value for the analysis time window, which is used to adjust the motor current signal prior to determining flow. For example, in some embodiments the measured motor current signal may be adjusted using the following equation:

$$adj_{mc}=MC+(Min_{mc}-C),$$

where MC is the pump motor current, C is the expected motor current at the maximum flow for the current pump speed, $Mim_{mc}$ is the measured minimum motor current within the analysis time window, and $adj_{mc}$ is the adjusted motor current signal that can then be used to calculate flow through the pump.

In some embodiments of the present technology it is assumed that the shape of the flow curve used to determine flow during operation of the pump is the same for a given motor speed across all pumps of the same design (e.g., the design shown in FIGS. 1A and 1B). Accordingly, a common set of flow curves may be used to calculate flow based on measured motor current, and adjusting the motor current based on a determined offset value as described herein can be accomplished by shifting a flow curve at the current speed of the motor to the right or left along the motor current axis, and then using the values in the shifted flow curve to perform the flow calculation.

Figure 7:
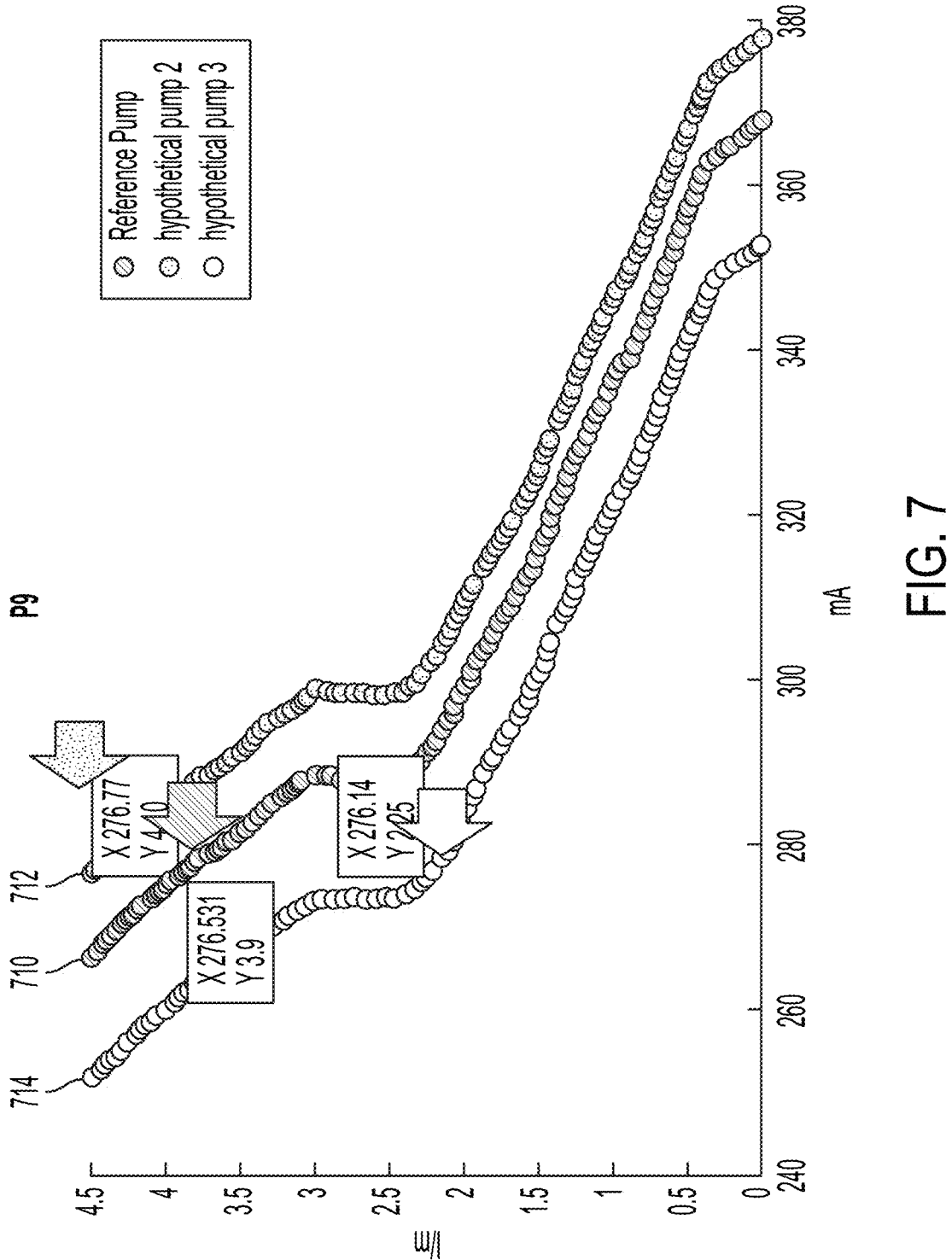
FIG. 7 schematically illustrates shifting a flow curve based on a determined offset value in accordance with some embodiments of the present technology.

Shifting a flow curve by applying an offset value in accordance with some embodiments is shown schematically in FIG. 7. A reference flow curve 710 may have been determined, for example, based on offline analysis of a plurality of pumps during which flow and/or motor current were measured during testing to derive the values in the flow curve. Flow curve 712 illustrates an example of a hypothetical flow curve associated with a pump during operation. As shown, flow curve 712 is located to the right of flow curve 710 in the plot such that the same motor current value corresponds to less flow for the reference pump compared to the operating pump. Accordingly, if the motor current signal was not adjusted in this situation, it would be assumed that flow curve 710 is correct and the flow calculation would be incorrectly low. It should be appreciated that due to the steepness of the flow curves, even small differences in measured versus expected motor current can lead to large differences in the flow calculation.

Using the techniques described herein, including the assumption that the flow curve shape remains constant across pumps, an offset value can be calculated and the flow curve 712 can be shifted to the left to the position of flow curve 710. For instance, within an analysis time window, the minimum motor current may be determined, which corresponds to the uppermost point of flow curve 712 (maximum flow). In the example of FIG. 7, this value is about 280 mA. The expected motor current value corresponding to maximum flow is the uppermost point of flow curve 710, which is shown in FIG. 7 as about 270 mA. Accordingly, in the example of FIG. 7, the offset value is 280 mA–270 mA=10 mA. Accordingly, flow curve 712 may be shifted to left the appropriate amount by subtracting the offset value of 10 mA from each of the data points in flow curve 712.

Figure 8:
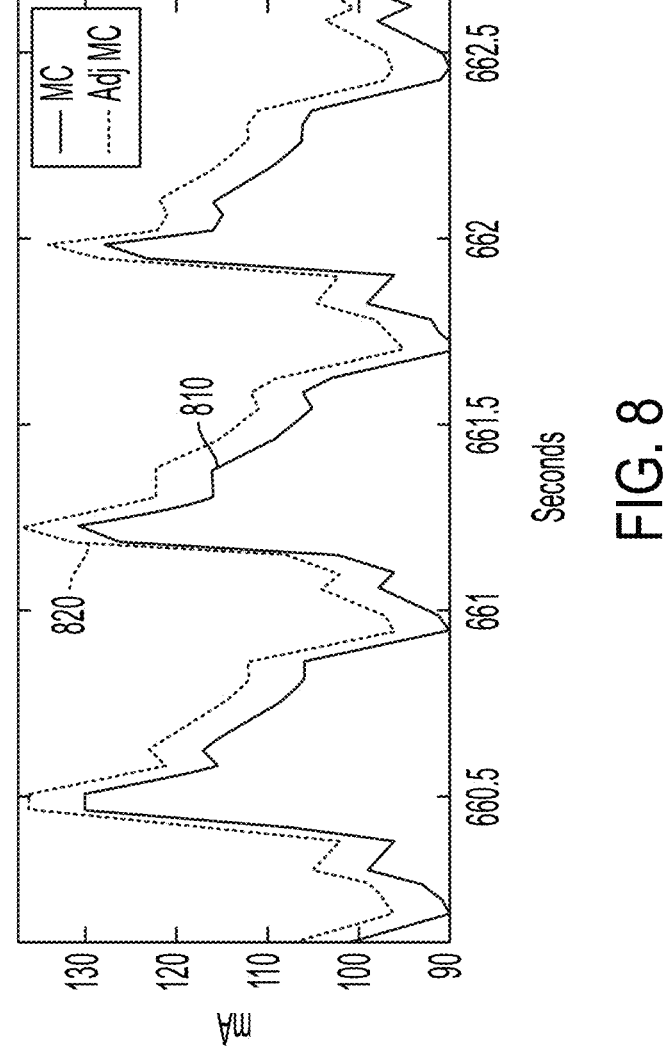
FIG. 8 illustrates a result of adjusting the motor current of a pump system by applying an offset value to the measured motor current in accordance with some embodiments of the present technology.

Flow curve 714 shows another hypothetical curve 714 in which the measured value of the motor current corresponding to maximum flow is lower than the expected value associated with flow curve 712, which would result in the flow calculation being incorrectly high if the motor current was not adjusted. For instance, without motor current adjustment, a measured motor current of 280 mA results in a flow of approximately 4 l/min based on the reference flow curve 710, whereas the actual flow based on flow curve 714 is substantially lower at about 2.25 l/min. To adjust the motor current prior to calculating flow, flow curve 714 may be shifted to the right by applying an offset value determined using the techniques described herein. For instance, within an analysis time window, the minimum motor current may be determined, which corresponds to the uppermost point of flow curve 714 (maximum flow). In the example of FIG. 7, this value is about 250 mA. The expected motor current value corresponding to maximum flow is the uppermost point of flow curve 710, which is shown in FIG. 7 as about 270 mA. Accordingly, in the example of FIG. 7, the offset value is 250 mA−270 mA=−20 mA. Accordingly, flow curve 714 may be shifted the appropriate amount to the right by adding the offset value of 20 mA (e.g., by subtracting the offset value of −20 mA) from each of the data points in flow curve 714. By shifting the flow curve 714 to the right, the measured motor current signal may be adjusted upwards as shown in FIG. 8. In particular, FIG. 8 shows the measured motor current signal 810 and the adjusted motor current signal 820 after taking into account the offset value using the techniques described herein. In this way, the measured motor current can be continuously adjusted prior to flow calculation to provide more accurate flow calculations based on the motor current signal.

Continuous adaptation of the measured pump motor current may be desired to accommodate for instabilities in the motor current signal due, for example, to reasons other than changes in flow through the pump. However, the inventors have recognized and appreciated that providing continuous adaptation of the motor current will only result in accurate flow calculations if the adjustments are made while pump is operating under normal conditions. As discussed above, there may be times during operation of a pump that the pump is not operating normally. Accordingly, some embodiments are directed to identifying such abnormal conditions and modifying the continuous motor current adaptation technique described herein to improve flow calculation during occurrence of such abnormal conditions. Modifying continuous motor current adaptation based on detection of abnormal events of pump operation is also referred to herein as "dynamic offset."

Figure 9C:
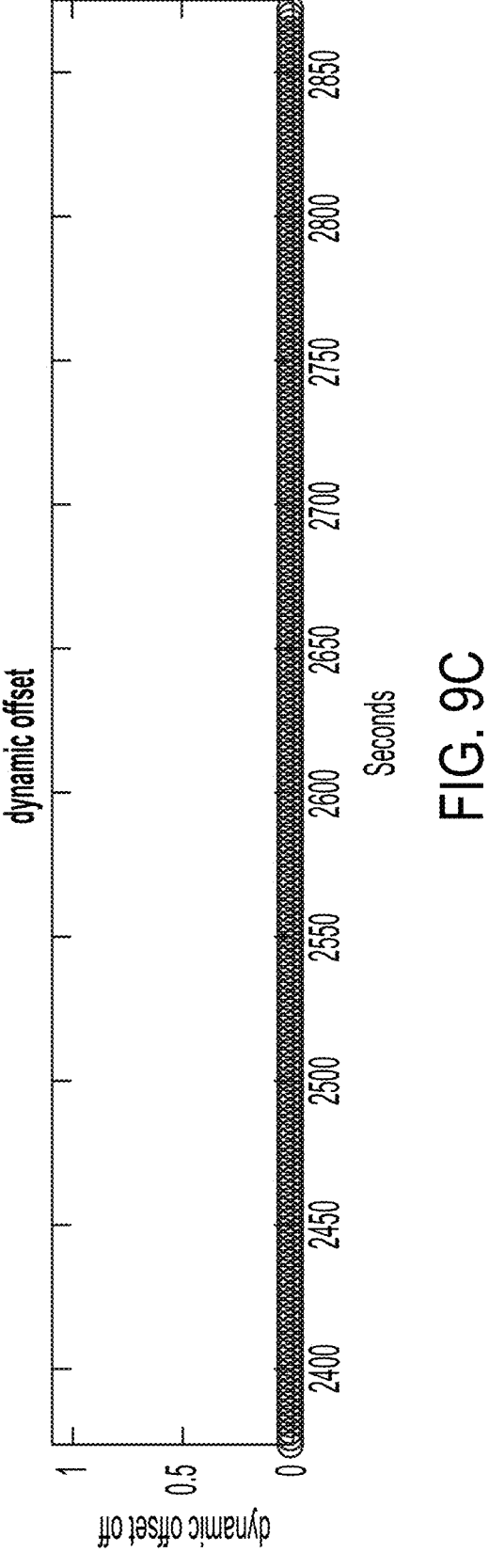

FIGS. 9A-9C illustrate the effect of keeping continuous motor current adjustment active during abnormal events, leading to an overestimation of flow while the abnormal event is occurring. FIG. 9A shows the motor current signal of a pump with motor current (mA) represented on the y-axis and time represented on the x-axis. As can be observed, over time there are characteristic changes in the motor current signal that represent the occurrence of abnormal events indicating that the pump is not operating normally. FIG. 9C shows that continuous adjustment of the motor current signal using the techniques described herein remained active regardless of whether abnormal events were detected. As shown in FIG. 9B, the arrows indicated points in time during which the calculated flow was overestimated when the pump experienced an abnormal event (e.g., a suction event), which prevented normal flow through the pump.

Figures 10A, 10B:
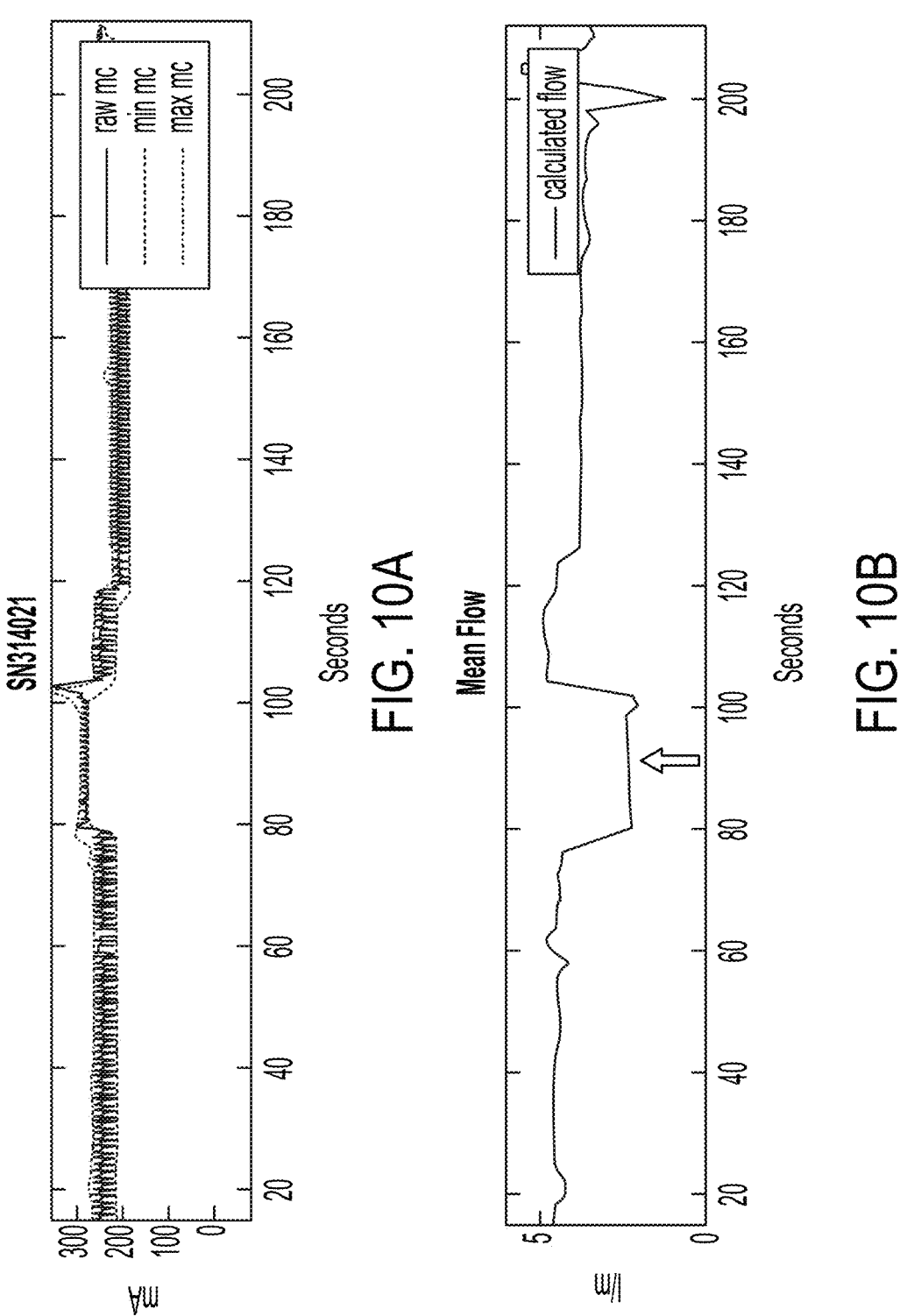
FIGS. 10A-10C illustrate a technique for more accurately calculating flow when a suction condition is detected in accordance with some embodiments of the present technology.
Figure 10C:
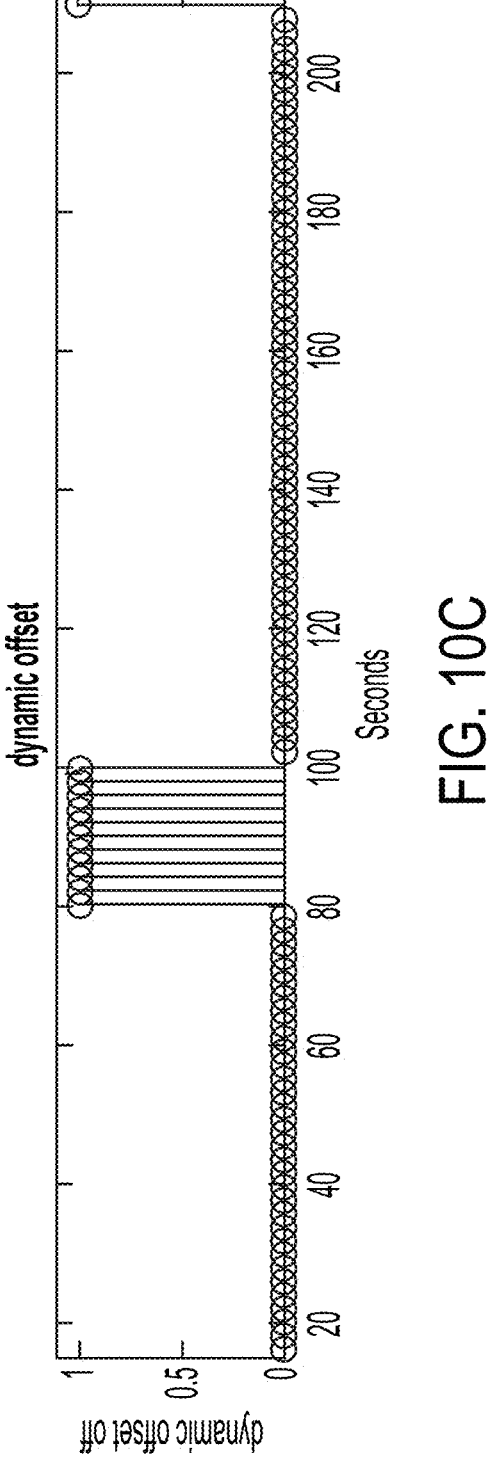

FIGS. 10A-10C illustrate the effect of modifying continuous motor current adjustment during abnormal events, resulting in a calculation of flow that would be expected during such events. FIG. 10A shows the motor current signal of a pump with motor current (mA) represented on the y-axis and time represented on the x-axis. As shown in FIG. 10A, over time there are characteristic changes in the motor current signal of FIG. 10A that represent the occurrence of abnormal events indicating that the pump is not operating normally. FIG. 10C shows that continuous adjustment of the motor current signal using the techniques described herein is modified (e.g., turned off or "anchored") during a detected abnormal event. As shown in FIG. 10B, the arrow indicates that turning off the motor current adaptation during occurrence of the detected abnormal event (e.g., a suction event), results in the calculated flow decreasing during the duration of the abnormal event, which is what would be expected due to the normal flow through the pump being disrupted.

Figures 11A, 11B:
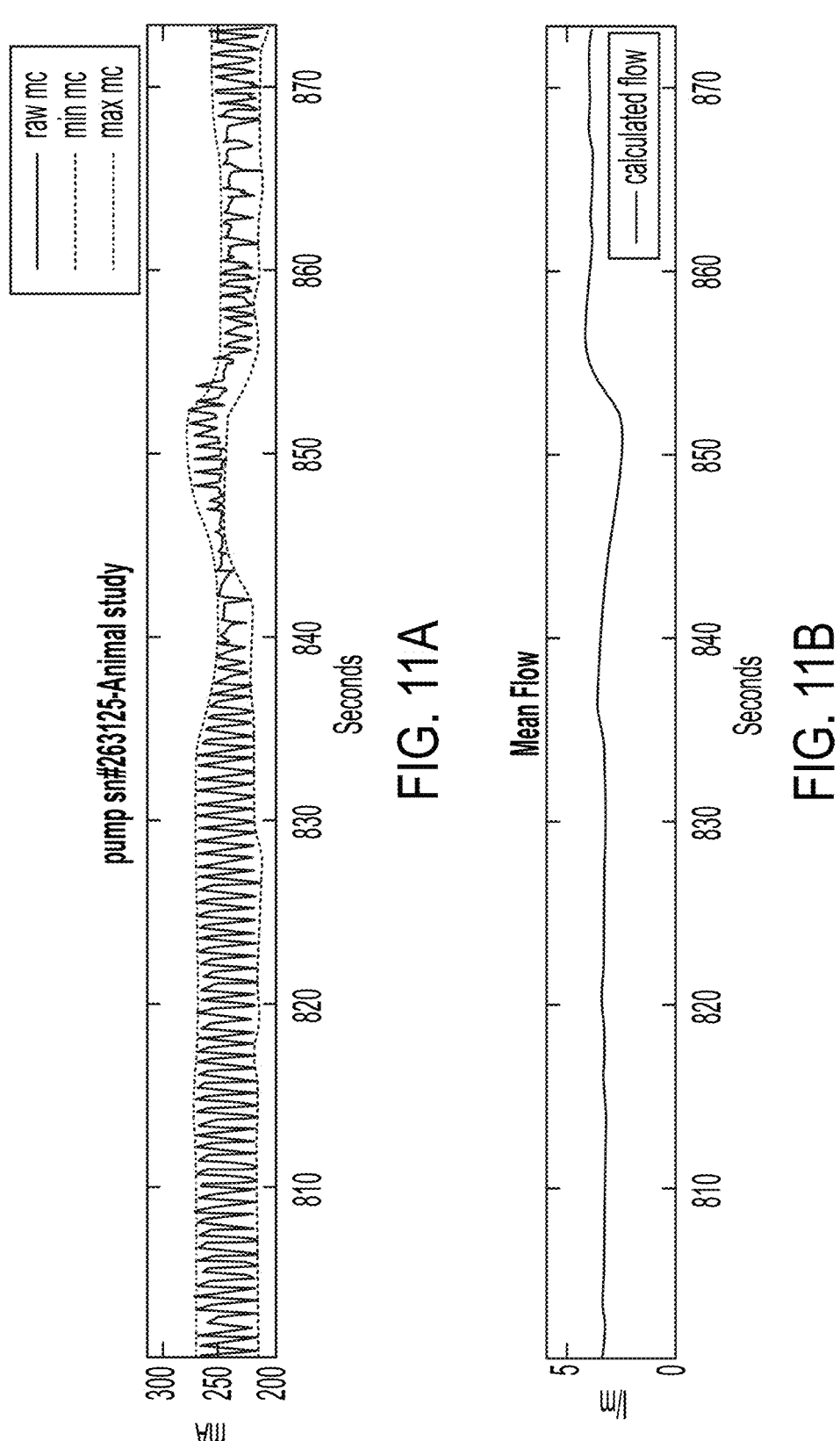
FIGS. 11A-11D illustrate a technique for more accurately calculating flow when a decoupling condition is detected in accordance with some embodiments of the present technology.
Figures 11C, 11D:
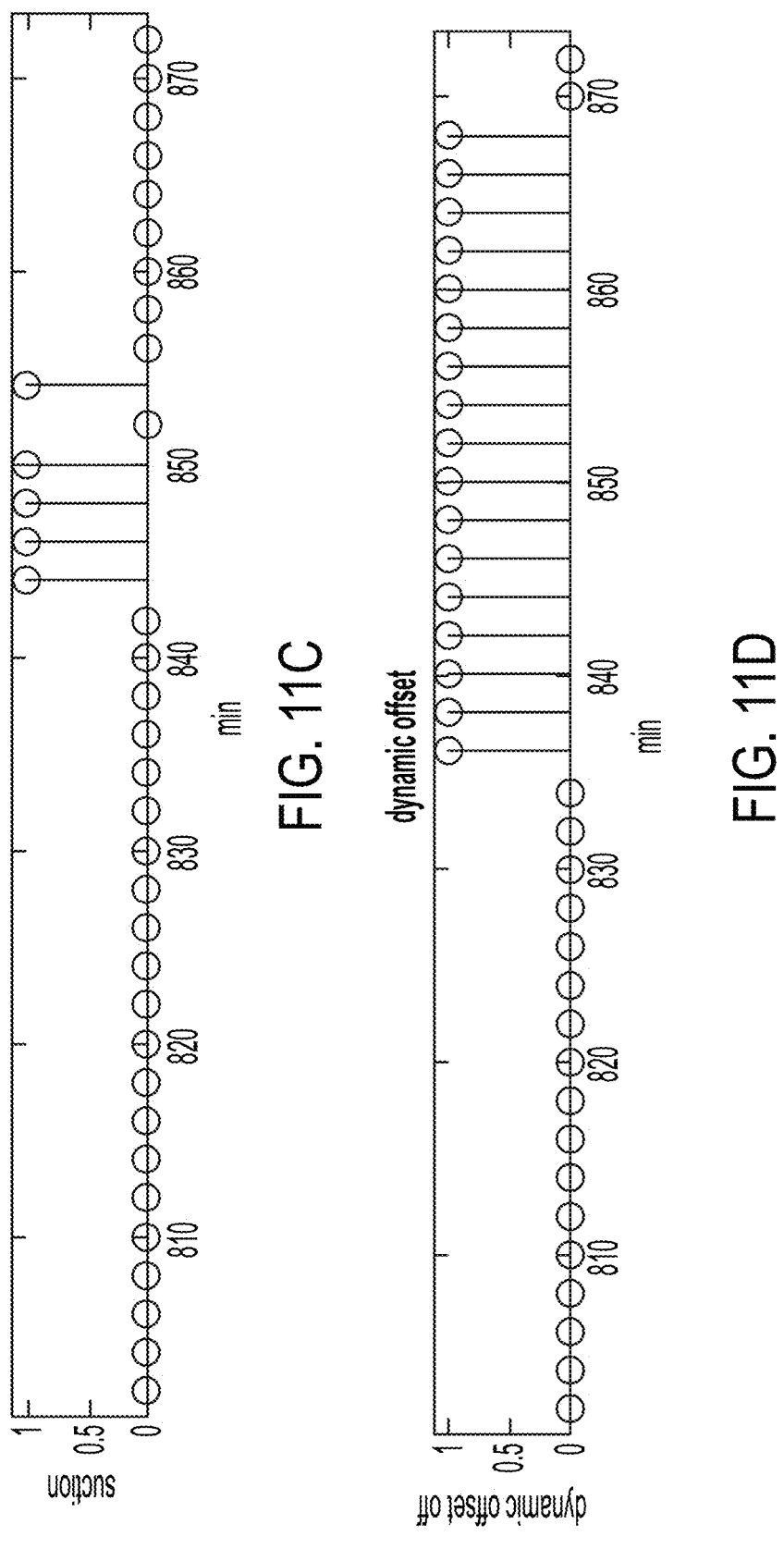

FIGS. 11A-11D illustrate another example of the effect of modifying continuous motor current adjustment during abnormal events, resulting in a calculation of flow that would be expected during such events. FIG. 11A shows the motor current signal of a pump with motor current (mA) represented on the y-axis and time represented on the x-axis. As shown in FIG. 11A, the motor current signal includes multiple types of abnormal events. Prior to a suction event starting around the 844 minute mark, a decoupling event as another type of abnormal event can be observed starting around the 836 minute mark. FIG. 11C illustrates the output of suction event detection logic indicating when the detection of a suction event is likely. FIG. 11D illustrates that to account for the presence of both the earlier decoupling event and the subsequent suction event, the continuous adjustment of the motor current signal using the techniques described herein is modified (e.g., turned off or "anchored") during both detected abnormal events. As shown in FIG. 10B, turning off the motor current adaptation during occurrence of the detected abnormal events, results in the calculated flow decreasing smoothly during the duration of the abnormal events, which is what would be expected due to the normal flow through the pump being disrupted.

Abnormal events including, but not limited to decoupling events and suction events, may be detected in any suitable way, examples of which are discussed below. In some embodiments, the motor current signal is analyzed to detect one or more metrics used to detect abnormal events. Such metrics include, but are not limited to a pulsatility index (PI) and a minimum bandpass signal (MBS).

Abnormal Event Detection Using Pulsatility Index

In one aspect of the present technology, a pulsatility index is used to detect an abnormal event such as suction event in a pump system (e.g., pump system 100). For example, in the field of medical ultrasound analysis of blood flow, the pulsatility index is defined as the difference between peak systolic and end-diastolic blood flow velocity, divided by the time-averaged flow velocity. Such a pulsatility index is postulated to reflect the vascular resistance in the arteries distal from the location of acoustic insulation. As described herein, the principles of the systolic and diastolic flow velocity pulsatility may be extended to the motor current signal of a blood pump to calculate a pulsatility index (PI) of the motor current and are used to detect suction events.

For example, in one aspect of the present technology, to calculate the PI of the motor current signal, the maximum motor current (max MC) and the minimum motor current (min MC) within a predetermined time duration window (predetermined window) are each detected by the processor 204. Also, the mean motor current (mean MC) is calculated by the processor 204 by averaging the motor current samples within the predetermined window:

$$\text{mean } MC = \sum_{i=0}^{N} \frac{MC(i)}{N}$$

where N represents the number of samples collected in the predetermined time window. In one aspect, the predetermined window is 2 seconds and the number of samples N collected in the predetermined time window is 500. The 2 second time window is selected to provide a balance between sensitivity and stability when used to detect a suction event using the techniques described herein. In this regard, a 2 second time window is sufficiently short to enable the method to be sensitive enough to detect a suction event, while also being sufficiently long to enable the method to be stable. It is to be appreciated that other time durations less than or greater than 2 seconds (e.g., 1 second, 5 second, etc.) for the predetermined window are contemplated to be within the scope of the techniques described herein.

With the max MC, min MC, and mean MC now calculated, the processor 204 calculates a normalized PI of the motor current signal as defined below:

$$PI = \frac{(\max\ MC) - (\min\ MC)}{\text{mean } MC}$$

When a suction event occurs, it causes the PI of the motor current to decrease and the minimum motor current to increase. For example, this effect is shown in the graph of FIG. 10A, where the minimum motor current line tracks the bottom of the pulsatile waveform corresponding to the raw motor current. As shown, the pulsatility of the raw motor current during a suction event is altered. In this regard, as shown in FIG. 10A, during a suction event, the PI of the motor current is decreased and the minimum motor current is increased relative to the minimum motor current measured outside (before and after) the suction event.

The decrease in pulsatility of the motor current exhibited during a suction event may be used to detect abnormal events, such as suction events, during operation of the pump. Since the calculated PI is normalized (by dividing by the mean motor current), a global threshold can be defined across all pump speeds and in view of the decreasing motor current over time. The global threshold may then be compared to a calculated PI of the motor current when the pump is in operation to detect if a suction event is occurring. For example, the threshold may be approximately (e.g., +/−10%) 0.15, although it should be appreciated that a different threshold may alternatively be used.

Abnormal Event Detection Using Normalized Minimum Bandpass Signal

An additional or alternate technique for detecting abnormal events such as suction events involves filtering the motor current signal using a band-pass filter that passes frequencies in a predetermined range, such as, 0.5 to 5 Hz. The predetermined range, e.g., 0.5 to 5 Hz, may be selected based on the typical heart beat frequency range of 30 to 300 beats per minute (BPM). It is to be appreciated that the predetermined range may be 0.5 to 3 Hz, 0.5 to 5 Hz, 0.5 to 8 Hz, 0.5 to 10 Hz, or any other suitable range that contains sufficient information regarding the pulsatility of the heartbeat of the patient. A range of 0.5 Hz to 5 Hz may balance sensitivity with stability when used to detect abnormal events as described in more detail below.

The band-pass filtering is analogous to extracting pulsatility information from the motor current signal assuming the typical heartbeat range of 30 to 300 BPM. The band-pass filter may be implemented as a digital filter (e.g., filter software that may be stored in memory 202 and executed by processor 204) applied by processor 204. Alternatively, processor 204 may control one or more analog filter circuits (including a suitable band-pass filter), for example, included in control unit 200 or external to control unit 200, to band-pass filter the motor current signal. In yet further embodiments, a combination of analog and digital filters may be used to implement the band-pass filter.

In one aspect, the band-pass filter may be a sixth-order elliptic filter that passes frequencies in the predetermined range, e.g., 0.5 to 5 Hz. As described above, normalization of the signals used in the abnormal event detection techniques described herein allows the use of absolute thresholds to detect such events even though the motor current may vary (e.g., trend downward) over time. Accordingly, the band-pass filtered signal may also be normalized. For example, in one aspect, the processor 204 normalizes the band-pass signal according to the following equation:

$$\text{normalized bandpass filtered signal} = \frac{MC(\text{bandpass}(i))}{MC(\text{lowpass}(i))}$$

$$i = 0 \text{ to } N$$

where, the equation is performed as a point-by-point operation such that each sample i of the band-pass filtered signal (MC(bandpass(i))) is divided by each sample i of the low-pass filtered signal (MC(lowpass(i))) to generate the normalized band-pass signal.

The processor 204 then calculates a normalized minimum band-pass signal index (herein referred to as the MBS index) by detecting a minimum value of the normalized band-pass filtered signal within a predetermined window of the signal and evaluating the MBS index relative to a threshold. In one aspect, the absolute value of the detected minimum value within the predetermined window (i.e., abs(MBS)) is compared to the threshold value. Using the absolute value of MBS may facilitate the determination of abnormal events such as events from the motor current signal.

In some embodiments, both the PI of the motor current and the MBS index described above are combined to detect abnormal events. The combination of the PI and MBS index in a single method may produce even more sensitive and stable results for abnormal event detection. There is often a trade-off between sensitivity and specificity in the abnormal event detection techniques described herein. In this regard, increasing the sensitivity of a detection technique can decrease its specificity.

Figure 12:
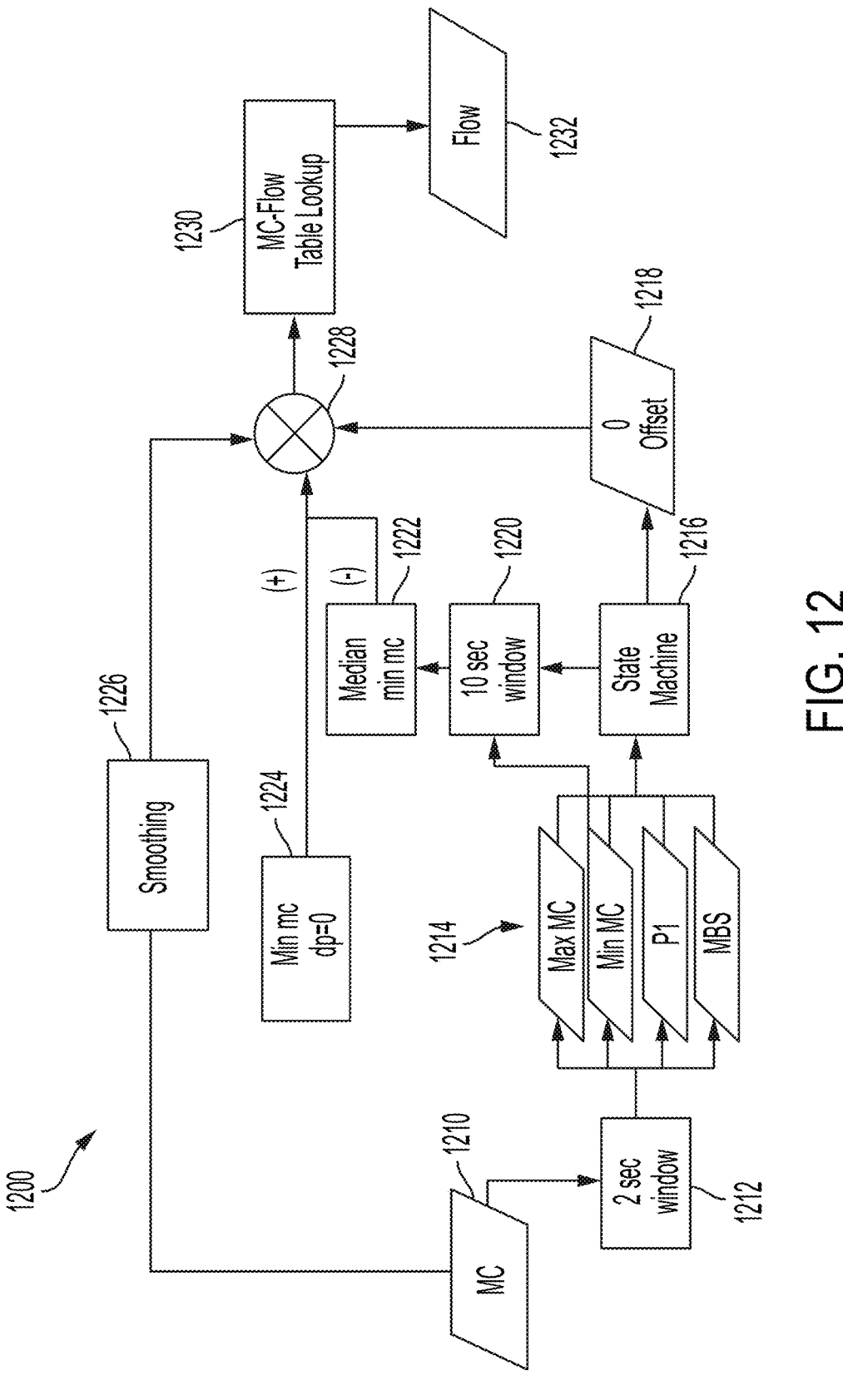
FIG. 12 illustrates a flowchart of a process for adapting a motor current signal used to determine flow through a pump system in accordance with some embodiments of the present technology.

FIG. 12 illustrates a flowchart of an example process 1200 for continuous adaptation of motor current used to calculate flow through a mechanical circulatory support device (e.g., pump 100) in accordance with some embodiments. In act 1210, the motor current (MC) signal is received from a motor of the pump during operation. Process 1200 then proceeds to act 1212, where a 2 second window of the motor current signal is extracted for analysis. As discussed above in connection with act 320 in FIG. 3, any suitable length of time window may be used, and the example of using a 2 second window in process 1200 is not limiting.

Process 1200 then proceeds to act 1214, where the motor current signal within the 2 second window is analyzed to determine one or more characteristics of the motor current signal, examples of which include, but are not limited to, maximum MC, minimum MC, pulsatility index (PI) and minimum bandpass signal (MBS). One or more of the determined characteristics are then provided as input to state machine 1216. State machine 1216 is configured to process the values input from act 1214 and determine whether an abnormal event has occurred (e.g., by comparing the input values to one or more thresholds). For example, determining whether an abnormal event has occurred is discussed in connection with act 330 above. In some embodiments, at least some of the characteristics determined in act 1214 may be used to determine other characteristics or metrics used to detect abnormal events. For example, maximum MC and minimum MC may be used to determine PI and/or MBS as described above. Additionally or alternatively, one or more characteristics (e.g., PI, MBS) determined in act 1214 may be provided directly to state machine 1216 for abnormal event detection. In some embodiments, state machine is implemented as a finite-state machine model, where the offset value used to adjust the motor current is scalar controlled (anchor vs. update) by one or both of the PI and MBS values provided as input to the state machine.

If it is determined by state machine 1216 that an abnormal event has occurred (e.g., based on one or both of PI and MBS), process 1200 proceeds to act 1218, where an offset value is not determined (or alternatively the offset value is set to 0). Process 1200 then proceeds to acts 1220 and 1222 where an offset value for the motor current adaptation process is determined, for example, as discussed previously in connection with act 340 of process 300. As shown, some embodiments store a plurality of previously-determined offset values in a buffer (e.g., corresponding to a 10 second window of the motor current signal), and a median value of the values stored in the buffer may be selected in act 1222 as the offset value to use for adapting the motor current.

The motor current signal 1210 may be adapted in act 1228 based on the results of the previous acts in process 1200. Adapting the motor current signal based on a determined offset value is discussed in more detail herein in connection with act 350 of process 300. As shown, in some embodiments, the motor current signal 1210 may be smoothed (e.g., filtered using a low-pass filter) in act 1226 prior to adaptation in act 1228. During adaptation in act 1228, the offset value (e.g., either based on the median minimum motor current in the buffer or 0) is subtracted from the minimum motor current when the differential pressure between the inlet and outlet of the pump is minimum (dp=0, shown as element 1224 in process 1200), which as discussed above corresponds to time point at which the flow through the pump is maximum (during systole). That value is then added to the smoothed motor current signal in act 1228 to produce the adjusted motor current signal. Process 1200 then proceeds to act 1230, where the adjusted motor current signal is used to determine the flow through the pump using stored data that relates motor current to flow (e.g., the flow curves described above in connection with FIG. 5). Determining flow based on the adjusted motor current is described in more detail herein in connection with act 360 of process 300.

Process 1200 then proceeds to act 1232, where the flow determined in act 1230 is provided as output (e.g., to a user). In some embodiments, the calculated flow determined in act 1232 may be used to change an operation of control unit 200. For instance, an indication of the calculated flow may be provided via user interface 206 of control unit 200 as described herein in connection with FIG. 1A. The indication of the calculated flow may be provided in any suitable way. For instance, a numerical value indicating the flow may be provided on a display associated with the user interface. Additionally or alternatively, a graphical value indicating the flow may be displayed, one or more visual indicators (e.g., one or more lights such as LEDs) may be activated based on the calculated flow, or one or more auditory signals may be provided to indicate the calculated flow. In some embodiments, the calculated flow may be used to control one or more operations of the pump itself (e.g., by changing an operation of motor 150). In such embodiments, the continuous motor current adaptation provided by the present technology may provide feedback control of the pump that enables the flow to remain within specified bounds thereby optimizing the flow for individual patients.

Having thus described several aspects and embodiments of the technology set forth in the disclosure, it is to be appreciated that various alterations, modifications, and improvements will readily occur to those skilled in the art. For example, while aspects of the present technology relate to an apparatus and methods for detection, separation, purification, and/or quantification of bacteria as described herein, the inventors have recognized that such apparatus and methods are broadly applicable to other organisms of interest, e.g. viruses, yeast, and aspects of the technology are not limited in this respect.

Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. A method of determining flow through a circulatory support device, the method comprising:

receiving a motor current signal measured from a motor of the circulatory support device during operation;

determining within a time window of the motor current signal, a measured motor current value at which flow through the circulatory support device is maximum;

determining an offset value based, at least in part, on the measured motor current value;

determining based, at least in part, on the received motor current signal, whether an abnormal condition has occurred;

adjusting the motor current signal measured from the motor based, at least in part, on the offset value and the determination of whether an abnormal condition has occurred to produce an adjusted motor current signal; and determining the flow through the circulatory support device based, at least in part, on the adjusted motor current signal.

2. The method of claim 1, wherein the measured motor current value is a maximum motor current value or a minimum motor current value within the time window.

3. The method of claim 2, wherein the measured motor current value is the minimum motor current value within the time window.

4. The method of claim 1, wherein a length of the time window is between one and four seconds.

5. The method of claim 1, wherein determining the offset value is further based, at least in part, on a speed of the motor.

6. The method of claim 5, further comprising:

storing, on at least one storage device, data relating flow values to motor current values for each of a plurality of motor speeds, and wherein determining the offset value comprises:

determining based, at least in part, on the stored data, an expected motor current value associated with a maximum flow at the speed of the motor; and determining the offset value as a difference between the motor current value and the expected motor current value.

7. The method of claim 6, wherein adjusting the motor current signal comprises adding the offset value to the motor current signal to produce the adjusted motor current signal.

8. The method of claim 6, wherein determining the flow through the circulatory support device comprises:

determining the flow further based, at least in part, on the stored data relating flow values to motor current values at the speed of the motor.

9. The method of claim 1, wherein adjusting the motor current signal based, at least in part, on the offset value and the determination of whether an abnormal condition has occurred to produce an adjusted motor current signal comprises using an offset value of zero when it is determined that an abnormal condition has occurred.

10. The method of claim 9, wherein determining whether an abnormal condition has occurred comprises determining whether the circulatory support device is in a suction state or a decoupling state.

11. The method of claim 1, further comprising:

storing previously determined offset values in a buffer; and storing the determined offset value in the buffer.

12. The method of claim 11, wherein the each of the previously determined offset values in the buffer is a scaled offset value scaled based on a speed of the motor at the time when the offset value was determined, and wherein storing the determined offset value in the buffer comprises:

scaling the determined offset value based on the speed of the motor; and storing the scaled determined offset value in the buffer.

13. The method of claim 11, wherein adjusting the motor current signal comprises adjusting the motor current signal based, at least in part, on a median value of the previously determined offset values in the buffer.

14. The method of claim 13, wherein adjusting the motor current signal comprises:

transforming the median value based on a present speed of the motor; and adjusting the motor current signal based on the transformed median value.

15. The method of claim 11, further comprising:

storing the determined offset value in the buffer only when it is determined that an abnormal condition has not occurred.

16. The method of claim 1, further comprising:

filtering the received motor current signal, and wherein adjusting the motor current signal comprises adjusting the filtered motor current signal.

17. The method of claim 1, further comprising:

displaying on at least one graphical user interface, an indication of the determined flow through the circulatory support device.

18. The method of claim 1, further comprising displaying on at least one graphical user interface, a numerical value of the determined flow and/or a graphical value indicating the determined flow.

19. A circulatory support device, comprising:

a rotor;

a motor configured to drive rotation of the rotor at one or more speeds; and at least one controller configured to:

receive a motor current signal measured from the motor;

determine within a time window of the motor current signal, a measured motor current value at which flow through the circulatory support device is maximum;

determine an offset value based, at least in part, on the measured motor current value;

determine based, at least in part, on the received motor current signal, whether an abnormal condition has occurred;

adjust the motor current signal measured from the motor based, at least in part, on the offset value and the determination of whether an abnormal condition has occurred to produce an adjusted motor current signal; and determine the flow through the circulatory support device based, at least in part, on the adjusted motor current signal.

20. A controller for a circulatory support device, the controller comprising:

at least one hardware processor configured to:

receive a motor current signal measured from a motor of the circulatory support device;

determine within a time window of the motor current signal, a measured motor current value at which flow through the circulatory support device is maximum;

determine an offset value based, at least in part, on the measured motor current value;

determine based, at least in part, on the received motor current signal, whether an abnormal condition has occurred;

adjust the motor current signal measured from the motor based, at least in part, on the offset value and the determination of whether an abnormal condition has occurred to produce an adjusted motor current signal; and determine the flow through the circulatory support device based, at least in part, on the adjusted motor current signal.

* * * * *